United States Patent [19]

Sinnige et al.

[11] 4,247,692

[45] Jan. 27, 1981

[54] TRIAZINE DERIVATIVES

[75] Inventors: Hermannus J. M. Sinnige, Apeldoorn; Hendrik J. Hageman; Willem J. Mijs, both of Rozendaal; Stephanus A. G. de Graaf, Renkum, all of Netherlands; Vincent Oakes, St. Helens, England

[73] Assignee: Akzona Incorporated, Asheville, N.C.

[21] Appl. No.: 916,432

[22] Filed: Jun. 19, 1978

Related U.S. Application Data

[63] Continuation of Ser. No. 651,087, Jan. 21, 1976, abandoned.

[30] Foreign Application Priority Data

Jan. 25, 1975 [NL] Netherlands .................. 7500890

[51] Int. Cl.$^3$ .................. C07D 251/16; C07D 251/18; C07D 251/22; C07D 251/24
[52] U.S. Cl. .................. 544/194; 544/205; 544/206; 544/211; 544/213; 544/219; 544/216; 260/45.75 H; 260/45.8 NT; 544/207
[58] Field of Search .............. 544/194, 205, 206, 207, 544/211, 213, 216, 219

[56] References Cited

U.S. PATENT DOCUMENTS

| | | | |
|---|---|---|---|
| 2,394,526 | 2/1946 | Thurston et al. | 544/205 |
| 3,700,671 | 10/1972 | D'Alelio et al. | 544/219 |
| 4,124,763 | 11/1978 | Mijs et al. | 544/219 |

FOREIGN PATENT DOCUMENTS 954992  4/1964  United Kingdom .................. 544/219

OTHER PUBLICATIONS

Reimschuessel et al., Journal of Am. Chem. Soc. 82, 1960, p. 3759.

*Primary Examiner*—John D. Randolph
*Assistant Examiner*—Jane T. Fan
*Attorney, Agent, or Firm*—Francis W. Young; Robert F. Green

[57] ABSTRACT

Novel triazine derivatives which are with cyanoacetic acid, derivatives of cyanoacetic acid or malodinitrile substituted s-triazines and which provide stabilizers against ultraviolet radiation for organic polymers such as polyvinyl chloride or copolymers of polyvinyl chloride or polypropylene are obtained by reacting the corresponding chloro-s-triazinyl derivatives with sodium hydride or a metal lower alcoholate in an organic solvent, and isolating the resulting product by acidification.

28 Claims, No Drawings

TRIAZINE DERIVATIVES

This is a continuation of application Ser. No. 651,087, filed Jan. 21, 1976, now abandoned.

BACKGROUND OF THE INVENTION

The invention relates to novel U.V. stabilizers, processes for the preparation of these compounds, and the use of these compounds for stabilizing organic substances sensitive to U.V. radiation, and to products entirely or partly composed of substances thus stabilized.

Of numerous organic substances such as polymers, films, organic coatings, wax-like substances, resins, colorants and cosmetic preparations it is known that they may degrade under the influence of ultraviolet light. This degradation may manifest itself in various ways, such as in the deterioration of mechanical properties and color.

A large group of organic substances which are often exposed for a long time to daylight containing U.V. radiation is formed by both natural and synthetic polymers and by films and organic coatings. From the patent literature numerous compounds are known which may have a stabilizing influence on the degradation of organic substances exposed to ultraviolet light. In this connection mention is made of the Swiss Pat. Nos. 388 253, 396 831 and 396 832. Although the compounds mentioned in them have favorable properties, there is still found to be a great need for compounds which on the one hand can be prepared without difficulty and on the other hand display an even larger molar extinction and a more favorable absorption maximum in the ultraviolet radiation region of the solar spectrum.

It has now been found that said need may be provided for by incorporating in the polymers a stabilizing amount of one or more previously unknown compounds.

GENERAL DESCRIPTION OF THE INVENTION

According to one aspect of the present invention there are provided novel compounds having the general formula:

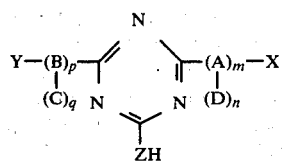

wherein m, n, p, and q are independently 0 or 1, provided that n=0 if m=0 and q=0 if p=0; when m=0, X is selected from the group consisting of chlorine, ZH, alkyl having 1 to 20 carbons atoms, alkenyl having 2 to 20 carbon atoms, cycloalkyl having 3 to 6 carbon atoms, and phenyl; when m=1 and n=0, X is selected from the group consisting of alkyl having 1 to 20 carbon atoms, alkenyl having 2 to 20 carbon atoms, cycloalkyl having 3 to 6 carbon atoms, and phenyl; when m=1 and n=1, X is selected from the group consisting of hydrogen, alkanoyl having 2 to 20 carbon atoms, benzoyl, benzene sulphonyl, amino, monoalkylamine having 2 to 8 carbon atoms, dialkylamino having 2 to 8 carbon atoms, phenylamino, alkyl having 1 to 20 carbon atoms, alkenyl having 2 to 20 carbon atoms, cycloalkyl having 3 to 6 carbon atoms, and phenyl; when p=0, Y is selected from the group consisting of ZH, alkyl having 1 to 20 carbon atoms, alkenyl having 2 to 20 carbon atoms, cycloalkyl having 3 to 6 carbon atoms, and phenyl; when p=1 and q=0, Y is selected from the group consisting of alkyl having 1 to 20 carbon atoms, alkenyl having 2 to 20 carbon atoms, cycloalkyl having 3 to 6 carbon atoms, and phenyl; when p=1 and q=1, Y is selected from the group consisting of hydrogen, alkanoyl having 2 to 20 carbon atoms, benzoyl, benzene sulphonyl, amino, monoalkylamino having 2 to 8 carbon atoms, dialkylamino having 2 to 8 carbon atoms, phenylamino, alkyl having 1 to 20 carbon atoms, alkenyl having 2 to 20 carbon atoms, cycloalkyl having 3 to 6 carbon atoms, and phenyl; when m=1 and n=1, A is nitrogen; when p=1 and q=1, B is nitrogen; when m=1 and n=0, A is oxygen or sulfur; when p=1 and q=0, B is oxygen or sulfur; when p=1 and q=1, C is selected from the group consisting of hydrogen, alkyl having 1 to 20 carbon atoms, alkenyl having 2 to 20 carbon atoms, cycloalkyl having 3 to 6 carbon atoms, and phenyl; when n=1 and m=1, D is selected from the group consisting of hydrogen, alkyl having 1 to 20 carbon atoms, alkenyl having 2 to 20 carbon atoms, cycloalkyl having 3 to 6 carbon atoms, and phenyl; the groups Y, B, and C being capable of forming a heterocyclic ring having 2 to 5 carbon atoms in which B represents the hetero nitrogen atom; the groups X, A, and D being capable of forming a heterocyclic ring having 2 to 5 carbon atoms in which A represents the hetero nitrogen atom; in all instances ZH represents a group which may lose a hydrogen atom in favor of an adjacent nitrogen atom of the triazine ring to form a desmotropic structure of the formula:

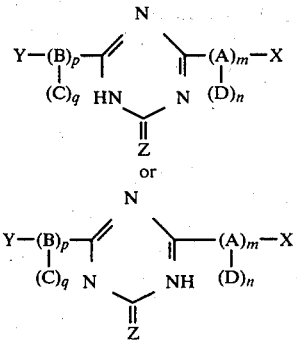

Z is in all instances a group of the formula

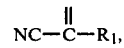

in which $R_1$ is selected from the group consisting of CN,

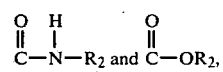

wherein $R_2$ is selected from the group consisting of hydrogen, alkyl, aralkyl, and cycloalkyl.

The foregoing compounds are with cyanoacetic acid, derivatives of cyanoacetic acid or malodinitrile substituted s-triazines.

A carboalkoxycyano-methyl-s-triazine derivative is known from an article by H. K. Reimschuessel et al. in the J. Am. Chem. Soc. 82 (1960) 3759. However, only mention is made of the preparation of the 2-carbo-ethoxy-cyano-methyl-4,6-dihydroxy-s-triazine, but nothing is said about the possible use of this compound as a U.V. stabilizer. This is not surprising in that this compound is particularly unstable in an acid medium, because it is immediately converted into 2,4-diketo-6(e-thoxy-carbonyl-cyano-methylene)-s-tri-hydro triazine, as also appears from the I.r. spectrum given in said article. The compound obtained contains some amide-like structural units, of which it is generally known that they are the cause of incompatability in most polymers.

Suitable substituents at $R_2$, X, Y, C and D in the foregoing formulas are to be considered as including all groups that do not have any unfavorable influence on the stabilizing effect and have a favorable influence on the compatibility between the stabilizing substance and the stabilized substance. As suitable substituents there may be mentioned fluorine, chlorine, bromine or iodine, hydroxyl, alkyl, aryl, alkoxy, alkylthio, carboxyl ester and cyano. Also functional groups, such as $-NH_2$, $-COOH$, and the like, may be present, so that the stabilizer can be incorporated in a particular polymer. Or use may be made of an $-SO_3H$ group, so that the stabilizer can be more readily emulsified in a particular product.

The choice of $R_2$, X, Y, C and D will generally be governed by the nature of the substances to be stabilized. The general aim is to have the stabilizing substances homogeneously distributed in the substance to be stabilized. If this is not quite possible and, for instance, segregation should occur, then it may be advisable to choose such substances in the stabilizer as will be chemically bound to the substance to be stabilized. This may be achieved for instance by choosing chlorine for X and/or Y and introducing into the substance to be stabilized free hydroxyl groups or amino groups, which will under properly chosen reaction conditions react with the triazine ring.

It is also possible to incorporate unsaturated groups in the stabilizer so that under the influence of a radical initiator the stabilizer can be linked to the ethylenically unsaturated groups in the substance to be stabilized.

If a compound is desired with a high molecular weight as well as with a high activity per unit weight, it may be of advantage to choose for $R_2$ a bifunctional alcohol such as ethylene glycol.

The compounds according to the invention are also particularly stable photochemically. Under conditions that may prevail when use is made of polymers that are very sensitive to peroxidic degradation, as in the case of polypropylene, it may be desirable to have these compounds additionally protected.

This may be accomplished by choosing for $R_2$, X and/or Y such groups as will also have the function of a primary or secondary antioxidant. As an example of a group having the function of a secondary anti-oxidant may be mentioned

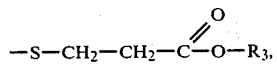

where $R_3$ may have the same meaning as indicated above for $R_2$. For $R_3$ one will preferably take an alkyl group with 1 to 20 C-atoms. Alternatively, a phenoxy group may be taken for $R_2$, X and/or Y, which phenoxy group is so substituted that it has the function of a primary antioxidant. As an example of such a phenoxy group may be mentioned the 4-hydroxy-3,5-diphenyl phenoxy group.

As the group $R_2$ has hardly any influence on the molar extinction or on the position of the absorption maximum in the U.V. region, it may be varied almost endlessly, provided that the stabilizer and the substance to be stabilized are well compatible with each other.

Some examples of novel triazine derivatives according to the invention are listed in the following table:

Table 1

1. (2,4-bis[diethylamino]-s-triazinyl-6-)methyl cyanoacetate
2. (2,4-dicyclohexylamino-s-triazinyl-6-)methyl cyanoacetate
3. (2,4-dipiperidino-s-triazinyl-6-)methyl cyanoacetate
4. (2,4-dihydrazino-s-triazinyl-6-)methyl cyanoacetate
5. (2,4-bis[2-hydroxyethylamino]-s-triazinyl-6-)-methyl cyano-acetate
6. (2-methoxy-4-diethylamino-s-triazinyl-6-)methyl cyanoacetate
7. (2-lauroxy-4-n-hexylamino-s-triazinyl-6-)methyl cyanoacetate
8. (2-methoxy-4-chloro-s-triazinyl-6-)-methyl cyanoacetate
9. (2-octoxy-4-chloro-s-triazinyl-6-)methyl cyanoacetate
10. (2-lauroxy-4-chloro-s-triazinyl-6-)methyl cyanoacetate
11. (2-stearoxy-4-chloro-s-triazinyl-6-)methyl cyanoacetate
12. 2,4-di(carbolauroxy cyanomethyl)-6-methoxy-s-triazine
13. 2,4-di(carbophenoxy cyanomethyl)-6-methoxy-s-triazine
14. 2,4-di(carbomethoxy cyanomethyl)-6-chloro-s-triazine
15. 2,4,6-tri(carbomethoxy cyanomethyl)-s-triazine
16. 2,4,6-tri(carbolauroxy cyanomethyl)-s-triazine
17. (2,4-dioctylmercapto-s-triazinyl-6-)methyl cyanoacetate
18. (2,4-dilaurylmercapto-s-triazinyl-6-)methyl cyanoacetate
19. (2,4-bis[2-carbomethoxyethylmercapto]-s-triazinyl-6-) methyl cyanoacetate
20. (2,4-bis[2-carbolauroxyethylmercapto]-2-triazinyl-6-) methyl cyanoacetate
21. (2-[3,5-diphenyl-4-hydroxy phenoxy]-4-methoxy-s-triazinyl-6) methyl cyanoacetate
22. (2,4-bis[3,5-diphenyl-4-hydroxy phenoxy]-s-triazinyl-6-) methyl cyanoacetate
23. (2,4-diallyl-s-triazinyl-6-)methyl cyanoacetate
24. (2,4-dimethyl-s-triazinyl-6-)methyl cyanoacetate
25. (2,4-di-n-octyl-s-triazinyl-6-)methyl cyanoacetate The new stabilizers according to the invention can be homogeneously incorporated in the substances to be stabilized, in the presence if desired of other additives such as softeners, pigments, heat stabilizers, primary and secondary antioxidants and mold release agents, use being made of known processing techniques such as mixing on the rolls. The amounts to be incorporated depend very much on the nature of the substances to be stabilized. Their total amount, however, will seldom be more than 10% by weight of the total amount of organic substance to be stabilized, said amount preferably being in the range of 0.1 to 5% by weight. The amounts used are as a rule in the range of 0.2 to 2% by weight.

Although the stabilizers according to the invention can be used in any organic substance sensitive to degradation under the influence of U.V. radiation, it has been found that the effectiveness per unit of weight of these compounds is greatest in the stabilization of polyolefins and especially of chlorinated organic compounds. In this connection special mention should be made of the favorable results obtained for polyvinyl chloride, and for all sorts of copolymers with vinyl chloride as their most important constituent, and for a small amount of other copolymerisable monomers such as copolymers of vinyl chloride and vinyl acetate, copolymers of vinyl chloride and vinylidene chloride, copolymers of vinyl chloride and acrylonitrile, copolymers of vinyl chloride with maleic acid or fumaric esters and copolymers of vinyl chloride with styrene. Favorable results have also been obtained for mixtures with a high percentage of polyvinyl chloride resin and a low percentage of another synthetic resin such as chlorinated polyethylene, copolymers of acrylonitrile, butadiene and styrene.

The novel compounds according to Formula (1) above may be obtained by causing a compound having the same general formula, wherein A, B, C, D, X, Y, m, n, p and q have the above-indicated meaning, neither X nor Y representing a phenyl group linked to the triazine ring by way of an oxygen or a sulphur atom, and where the group ZH has the meaning of a chlorine atom, to react in an organic solvent with the reaction product of sodium hydride or a metal alcoholate having not more than 18 carbon atoms and a compound of the formula: $CN-CH_2-R_1$ where $R_1$ has the above-indicated meaning, and isolating after acidification, one or more, depending on the number of desmotropic structures present, compounds having one or more of the formula (1), where Z has the meaning

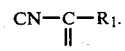

It has been found that if used is made of sodium hydride good results may be obtained if for the organic solvent dioxane or dimethoxy ethane is employed.

If use is made of a metal alcoholate, it is preferred that the organic solvent be benzene or toluene. It has also been found that the best results are obtained if for the metal alcoholate a sodium alcoholate with a lower alcoholate group such as sodium methylate or sodium butylate is used.

In the case where A and/or B represent(s) sulphur or oxygen and X and/or Y a substituted or non-substituted phenyl group, it is preferred to use a somewhat modified method of preparation. Such a method may, of course, also be used if X and/or Y does not have the meaning of a phenyl group, but has one of the other meanings indicated above.

The somewhat modified method of preparation consists in that a compound with the general formula according to (1) above where A, B, C, D, X, Y, m, n, p and q have the above-indicated meaning, and where the group ZH has the meaning of a chlorine atom, is brought into reaction in an organic solvent with the tetra-alkyl ammonium salt of the compound $CN-CH_2-R_1$, where $R_1$ has the above-indicated meaning, and one or more, depending on the number of desmotropic structures present, compounds obtained after acidification and having one or more of the general formula (1) are isolated.

For the tetra alkyl ammonium salt it is preferred to employ the tetra-n-butyl ammonium salt. Here too the use is possible of various compounds that are inert to the reaction components. It has been found that with advantage, use may be made of halogenated organic solvents. Preference is given to chloroform. Of the other solvents that may be used with favorable results there may be mentioned methylene chloride, carbon tetrachloride, 1,1,1-trichloroethane, tri- and perchloroethylene.

With either of the two above-mentioned methods of preparation the acidification may with advantage be carried using an inorganic acid such as hydrochloric acid.

In the preparation of the compounds according to the invention in which at least two chlorine atoms of the starting product cyanuric chloride have been replaced by at least two different substituents, the substituent

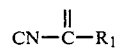

is usually introduced last. This is, of course, not an absolute necessity. It is also possible first to prepare a compound such as (2,4-dichloro-s-triazinyl-6-)methyl cyanoacetate, which may, if required, later on be provided with the desired substituents. In general, the sequence of substitution will be so chosen that the reactivity of the successive substituting agents will increase. The nature of these agents partly determines the magnitude of the yield.

After acidification the desired end product is still to be isolated. This may with advantage be done by extraction with a water-immiscible organic solvent. Favorable results are obtained with methylene chloride. After the solvent has been evaporated, the remaining crude end product may, if desired, be further purified by recrystallization from an appropriate solvent. As examples of suitable solvent there may be mentioned petroleum ether (boiling point 80°–100° C.), methanol, ethanol, a mixture of methanol and chloroform, etc. For a person skilled in the art it is not difficult empirically to determine the solvent or combination of solvents which is the most suitable for the recrystallization of a particular compound.

DESCRIPTION OF THE PREFERRED EMBODIMENTS

The invention will be further described in the following examples. The examples are, of course, given by way of illustration and should not be interpreted as limitative of the present invention.

EXAMPLE 1

Preparation of (2,4-dimethoxy-s-triazinyl-6-)methyl cyanoacetate

To a suspension of 134 g (1.6 moles) of sodium bicarbonate in a mixture of 400 ml of methanol and 40 ml of water were added 148 g (0.8 moles) of cyanuric chloride at 30° C.

After a reaction of 7 hours the reaction mixture was extracted with methylene chloride, followed by successively washing with water until neutral, drying with MgSO$_4$ and evaporating the solvent. After recrystallization from petroleum ether (boiling point 40°–60° C.) 126 g of 2,4-dimethoxy-6-chloro-s-triazine were obtained with a melting point between 74.2° and 76.2° C.

Subsequently, a suspension was prepared of 8.0 g (0.33 moles) of sodium hydroxide in 40 ml of dimethoxyethane. To it was added dropwise over a period of 10 minutes, with cooling in an ice bath, a solution of 33 g (0.33 moles) of methyl cyanoacetate in 60 ml of dimethoxyethane. After 1 hour 29.3 g (=0.167 moles) of 2,4-dimethoxy-6-chloro-s-triazine in 75 ml of dimethoxyethane were added to the reaction mixture dropwise at a temperature in the range of 20° to 25° C. After 1½ hours the mixture was poured into a dilute hydrochloric acid solution.

After extraction with methylene chloride, washing with water until neutral and drying over magnesium sulphate, the solvent was evaporated. Recrystallization from methanol resulted in obtaining 32.0 g of (2,4-dimethoxy-s-triazinyl-6-)methyl cyanoacetate in 82% yield.

The melting point of the compound was in the range of 166.3° to 167.2° C. The UV absorption in methanol was at $$\lambda_{max}^{CH_3OH} = 298 \; nm \; (\epsilon = 31,800)$$

EXAMPLE II

Preparation of (2,4-dioctoxy-s-triazinyl-6-)methyl cyanoacetate

To a solution of 18.1/g (0.1 mole) of cyanuric chloride and 26.0 g (0.2 moles) of octanol in 200 ml of dioxane were added 9.0 g (0.225 moles) of powdered sodium hydroxide over a period of 20 minutes at a reaction temperature in the range of 32° to 37° C. After 7 hours the reaction mixture was poured into 500 ml of petroleum ether (boiling point 40°–60° C.). The solution thus obtained was washed with water, dried with Mg SO$_4$ and the solvent evaporated.

The 2,4-dioctoxy-6-chloro-s-triazine was obtained in the form of an oil (26 g). Of this product 7.43 g (0.02 moles) were brought into reaction with the reaction product of 3.96 g (0.04 moles) of methyl cyanoacetate and 0.96 g (0.04 moles) of sodium hydride in the same way as indicated in Example I. After recrystallization from petroleum ether (boiling point 40°–60° C.) 6.1 g of (2,4-dioctoxy-s-triazinyl-6-)methyl cyanoacetate were obtained in 70% yield.

The melting point was 66.3°–68.9° C. The UV absorption maximum in methanol was at $$\lambda_{max}^{CH_3OH} = 299 \; nm \; (\epsilon = 27,000)$$

EXAMPLE III

Preparation of (2,4-dilauroxy-s-triazinyl-6-)methyl cyanoacetate 4.83 g (0.01 mole) of 2,4-dilauroxy-6-chloro-s-triazine prepared in the same way as indicated in Example II for the preparation of 2,4-dioctoxy-6-chloro-s-triazine were converted with the reaction product of 1.98 g (0.02 moles) of methyl cyanoacetate and 0.48 g (0.02 moles) of sodium hydride. After recrystallization from methanol 4.33 g of (2,4-dilauroxy-s-triazinyl-6-)methyl cyanoacetate having a melting point in the range of 85.8° to 86° C. were obtained in 80% yield. The UV absorption maximum in methanol was $$\lambda_{max}^{CH_3OH} = 298 \; nm \; (\epsilon = 29,900)$$

EXAMPLE IV

Preparation of (2,4-distearoxy-s-triazinyl-6-)methyl cyanoacetate.

The preparation was carried out in the same way as indicated in Example III for the preparation of the corresponding 2,4-dilauroxy compound.

The product was purified by recrystallization from petroleum ether (boiling point 80°–100° C.). The yield of the last step was 55%.

The melting point was in the range of 96.3°–97.1° C. The UV absorption maximum in chloroform was $$\lambda_{max}^{CHCl_3} = 303 \; nm \; (\epsilon = 20,600)$$

EXAMPLE V

Preparation of (2,4-dimethoxy-d-triazinyl-6-)lauryl cyanoacetate 3.51 g (0.02 moles) of 2,4-dimethoxy-6-chloro-s-triazine were prepared as indicated in Example I. In the same manner as described in Example II the 2,4-dimethoxy-6-chloro-s-triazine was brought into reaction with the reaction product of 10.1 g (0.04 moles) of lauryl cyanoacetate and 0.96 g (0.04 moles) of sodium hydride. After extraction with petroleum ether (boiling point 40°–60° C.) 5.0 g of product were obtained in 64% yield and with a melting point in the range of 96.0°–96.8° C. The UV absorption maximum in methanol was $$\lambda_{max}^{CH_3OH} = 299 \; nm \; (\epsilon = 26,100)$$

EXAMPLE VI

Preparation of (2,4-dimethoxy-s-triazinyl-6-)benzyl cyanoacetate 3.51 g (0.02 moles) of the 2,4-dimethoxy-6-chloro-s-triazine prepared in Example I were brought into reaction with the reaction product of 7.0 g (0.04 moles) of benzyl cyanoacetate and 0.96 g of (0.04 moles) of sodium hydride in the same way as indicated in Example II.

After recrystallization from methanol there were obtained 5.32 g (in 85% yield) of (2,4-dimethoxy-s-triazinyl-6-)benzyl cyanoacetate with a melting point in the range of 172.0° and 172.5° C. The UV absorption maximum in methanol was $$\lambda_{max}^{CH_3OH} = 299 \; nm \; (\epsilon = 24,100)$$

EXAMPLE VII

Preparation of (2,4-dioctoxy-s-triazinyl-6-)benzyl cyanoacetate 7.43 g (0.02 moles) of 2,4-dioctoxy-6-chloro-s-triazine were prepared in accordance with Example II and converted in the same way as indicated in said example by reacting it with the reaction product of 7.0 g (0.04 moles) of benzyl cyanoacetate and 0.96 g of (0.04 moles) of sodium hydride. After recrystallization from petroleum ether (boiling point 40°–60° C.) 5.1 g of the end product was obtained in 50% yield.

The melting point was in the range of 59.2°–60.4° C. The UV absorption maximum in methanol was $$\lambda_{max}^{CH_3OH} = 300 \; nm \; (\epsilon = 33,400)$$

EXAMPLE VIII

Preparation of (2,4-dimethylthio-s-triazinyl-6-)methyl cyanoacetate

To a suspension of 14.7 g (0.175 moles) of sodium bicarbonate in a solution of 15.8 g (0.086 moles) of cyanuric chloride in 70 ml of acetone there were added 20 ml of water at −5° C. To this mixture were added 8.4 g (0.175 moles) of methyl mercaptan at a temperature of 0° C. The reaction time was 9 hours and the temperature was allowed to rise to 20° C.

After the reaction mixture has been poured into water, it was extracted with ether. After washing with water, drying with Na$_2$SO$_4$ and evaporating the solvent, the crude product was purified by recrystallization from petroleum ether (boiling point 40°–60° C.). In this way 12.2 g of 2,4-dimethylthio-6-chloro-s-triazine were obtained in 69% yield. The melting point was in the range of 83.6°–84.4° C. In the way indicated in Example II, 2.08 g (0.01 mole) of the 2,4-dimethylthio-6-chloro-s-triazine thus prepared were reacted with 1.98 g (0.02 moles) of methyl cyanoacetate in the presence of 0.48 g (0.02 moles of sodium hydride.

After purification by recrystallization from methanol 2.15 g of (2,4-dimethylthio-s-triazinyl-6-)methyl cyanoacetate were obtained in 84% yield. The melting point was in the range of 185.0°–185.3° C. and the UV absorption maximum in methanol were $$\lambda_{max}^{CH_3OH} = 288 \; nm \; (\epsilon = 23{,}000) \text{ and } 301 \; nm \; (\epsilon = 26{,}200)$$

EXAMPLE IX

Preparation of (2,4-diphenoxy-s-triazinyl-6-)methyl cyanoacetate

To a solution of 18.4 g (0.1 mole) of cyanuric chloride in 90 ml of acetone was added dropwise a solution of 19.0 g (0.2 moles) of phenol and 8.0 g (0.2 moles) of sodium hydroxide in 75 ml of water at a reaction temperature in the range of 15° to 20° C. After 4½ hours the precipitate formed was removed by suction, washed with water and dried (with Mg SO$_4$). Purification by recrystallization from n-heptane gave 24.7 g of 2,4-diphenoxy-6-chloro-s-triazine in 82% yield. The melting point was 119°–121° C.

To 3.0 g (0.01 mole) of the last-mentioned product in 20 ml of chloroform was added dropwise, over a period of 1 hour, a solution in 50 ml of chloroform of 6.8 g (0.02 moles) of the tetra-n-butyl ammonium salt. The last-mentioned salt was prepared by a method of Brändström, published in Acta Chem. Scand., 23, 2203 (1969).

The reaction mixture was subsequently washed with dilute hydrochloric acid and water, dried with Mg SO$_4$ and the solvent evaporated.

Treatment of the solid substance with methanol was followed by recrystallization from ethyl acetate. In this way 1.48 g of the (2,4-diphenoxy-s-triazinyl-6-)methyl cyanoacetate were obtained in 41% yield. The melting point was 192.0°–195.6° C. and the UV absorption maximum $$\lambda_{max}^{CH_3OH} = 302 \; nm \; (\epsilon = 33{,}000)$$

EXAMPLE X

Preparation of (2,4-bis[4-methoxyphenoxy-]-s-triazinyl-6-)methyl cyanoacetate

The preparation was carried out in accordance with Example IX. Starting from 3.5 g (0.01 mole) of 2,4-bis(4-methoxyphenoxy)-6-chloro-s-triazine and 6.8 g (0.02 moles) of tetra-n-butyl ammonium salt of methyl cyanoacetate followed by recrystallization from dioxane, led to obtaining 3.04 g of (2,4-bis[4-methoxyphenoxy-]-s-triazinyl-6-)methyl cyanoacetate in 72% yield. The melting point was 187.6°–189.8° C. The UV absorption maximum was $$\lambda_{max}^{CH_3OH} = 303 \; nm \; (\epsilon = 29{,}000)$$

EXAMPLE XI

Preparation of (2,4-diphenyl-s-triazinyl-6)methyl cyanoacetate

To a solution of 46.0 g (0.25 molew) of cyanuric chloride in 300 ml of benzene there was added dropwise, over a period of 2 hours, a solution of phenyl magnesium bromide.

The last-mentioned solution was prepared by reaction of 94.2 g (0.6 moles) of bromobenzene and 16.4 g (0.6 moles) of magnesium in 200 ml of ether. After 1 day at room temperature the solvent was evaporated and the residue extracted with boiling petroleum ether (boiling point 80°–110° C.). As a result of cooling 2,4-diphenyl-6-chloro-s-triazine crystallized out; and recrystallization from a mixture of benzene and ethanol led to obtaining 36.8 g with a melting point in the range of 136.3°–137.4° C.

In the way indicated in Example II, 5.0 g (0.0187 moles) of this product were reacted with the reaction product of 3.7 g (0.0374 moles) of methyl cyanoacetate and 0.9 g (0.0374) moles of sodium hydride.

After recrystallization from a mixture of methanol and chloroform 3.62 g of the above product were obtained in 59% yield. The melting point was 237.2°–241.2° C. and the UV absorption maxima were $$\lambda_{max}^{CH_3OH} = 310 \; nm \; (\epsilon = 31{,}500) \text{ and } 380 \; nm \; (\epsilon = 1{,}950)$$

EXAMPLE XII

Preparation of (2,4-dimethoxy-s-triazinyl-6-)malodinitrile

To a suspension of 1.44 g (0.06 moles) of sodium hydride in 15 ml of dimethoxy ethane was added dropwise a solution of 3.96 g (0.06 moles) of malodinitrile in 15 ml of dimethoxy ethane. After 30 minutes there was added to it dropwise a solution in 30 ml of dimethoxy ethane of 5.26 g (0.03 moles) of 2,4-dimethoxy-6-chloro-s-triazine prepared in the same way as indicated in Example I. After 2 hours the solvent was evaporated and dilute hydrochloric acid was added.

After the precipitate had been removed by suction, it was washed with water and extracted with methylene chloride. In this way 5.07 g of (2,4-dimethoxy-s-triazinyl-6-)malodinitrile were obtained in 82% yield.

The melting point was 194.4°–194.6° C. The UV absorption maximum was $$\lambda_{max}^{CH_3OH} = 298 \; nm \; (\epsilon = 31{,}500)$$

EXAMPLE XIII

Preparation of (2,4-dioctoxy-s-triazinyl-6-)malodinitrile

The preparation was carried out as indicated in Example XII. 7.43 g (0.02 moles) of the 2,4-dioctoxy-6- chloro-s-triazine prepared in Example II were brought into reaction with the reaction product of 2.64 g (0.04 moles) of malodinitrile and 0.96 g (0.04 moles) of sodium hydride. After the reaction mixture had been poured into dilute hydrochloric acid, the precipitate formed was removed by suction and dissolved in carbon tetrachloride. Washing with water, drying with MgSO$_4$, and evaporation were followed by recrystallization from petroleum ether (boiling point 80°-100° C.).

In this way 5.7 g of (2,4-dioctoxy-s-triazinyl-6-)malodinitrile were obtained in 63% yield. The melting point was 141.9°-142.9° C. The UV absorption maximum was at $$\lambda_{max}^{CH_3OH} = 299 \text{ nm } (\epsilon = 27,000)$$

EXAMPLE XIV

Preparation of (2,4-dilauroxy-s-triazinyl-6-)malodinitrile

In the way indicated in Example XII 4.83 g (0.01 mole) of 2,4-dilauroxy-6-chloro-s-triazine were converted with the reaction product of 1.32 g (0.02 moles) of malodinitrile and 0.48 g (0.02 moles) of sodium hydride. After recrystallization from methanol 3.0 g of 2,4-dilauroxy-s-triazinyl-6-)malodinitrile were obtained in 59% yield. The melting point was in the range of 130°-136° C. and the UV absorption maximum $$\lambda_{max}^{CH_3OH} = 294 \text{ nm } (\epsilon = 33,700)$$

EXAMPLE XV

Preparation of (2,4-distearoxy-s-triazinyl-6-)malodinitrile

The preparation was carried out in the way indicated in Example XIII. 9.77 g (0.015 moles) of 2,4-distearoxy-6-chloro-s-triazine were converted with the reaction product of 1.98 g (0.03 moles) of malodinitrile and 0.72 g (0.03 moles) of sodium hydride. After recrystallization from a mixture of petroleum ether (boiling point 80°-110° C.) and ethanol there were obtained 8.6 g of (2,4-distearoxy-s-triazinyl-6-)malodinitrile in 80% yield. The melting point was in the range of 126.2°-127.8° C. The UV absorption maximum was $$\lambda_{max}^{CHCl_3} = 303 \text{ nm } (\epsilon = 18,400)$$

EXAMPLE XVI

Preparation of (2,4-dimethylthio-s-triazinyl-6-)malodinitrile 3.12 g (0.015 moles) of 2,4-dimethylthio-6-chloro-s-triazine prepared in the manner indicated in Example VIII were converted with the reaction product of 1.98 g (0.03 moles) of malodinitrile and 0.72 g (0.03 moles) of sodium hydride in the same manner as indicated in Example XII. The reaction product was dissolved in ammonia; the solution obtained was filtered, acidified and the precipitate formed was filtered off. It was washed with water and subsequently dried. 2.1 g of (2,4-dimethylthio-s-triazinyl-6-)malodinitrile were obtained in 60% yield.

The melting point was 240°-255° C. (followed by decomposition). The UV absorption maximum was $$\lambda_{max}^{CH_3OH} = 305 \text{ nm } (\epsilon = 28,200)$$

EXAMPLE XVII

Preparation of (2,4-diphenoxy-s-triazinyl-6-)malodinitrile 3.0 g (0.01 mole) of the 2,4-di-phenoxy-6-chloro-s-triazine prepared in Example IX were, in the same way as indicated in Example XII, converted with the reaction product of 1.32 g (0.02 moles) of malodinitrile and 0.48 g (0.02 moles) of sodium hydride. In this way 2.63 g of (2,4-diphenoxy-s-triazinyl-6-)malodinitrile were obtained in 80% yield.

The product melted with decomposition at 240° C. The UV absorption maximum was $$\lambda_{max}^{CH_3OH} = 298 \text{ nm } (\epsilon = 34,000)$$

EXAMPLE XVIII

Preparation of 2,4-di-(carbomethoxycyanomethyl)-6-methoxy-s-triazine

The preparation was carried out in the same way as indicated in Example II. 2.70 g (0.015 moles) of 2-methoxy-4,6-dichloro-s-triazine were converted with the reaction product of 5.95 g (0.06 moles) of methyl cyanoacetate and 1.44 g (0.06 moles) of sodium hydride. After extraction with methanol and petroleum ether (boiling point 40°-60° C.) 3.74 g of 2,4-di-(carbomethoxycyanomethyl)-6-methoxy-s-triazine were obtained in 82% yield. The UV absorption maxima were at $$\lambda_{max}^{CH_3OH} = 278 \text{ nm } (\epsilon = 33,400) \ 311 \text{ nm } (\epsilon = 31,800)$$
$$330 \text{ nm } (\epsilon = 16,000)$$

EXAMPLE XIX

Preparation of (2,4-dimethoxy-s-triazinyl-6-)phenyl cyanoacetate

The preparation was carried out in the same way as indicated in Example I.

2.63 g (0.015) moles of 2,4-dimethoxy-6-chloro-s-triazine were converted with the reaction product of 4.85 g (0.03 moles) of phenyl cyanoacetate and 0.72 g (0.03 moles) of sodium hydride. After recrystallization from methanol 1.8 g of (2,4-dimethoxy-s-triazinyl-6-)phenyl cyanacetate were obtained in 43% yield. The melting point was 185.0°-185.2° C. and the UV absorption maximum $$\lambda_{max}^{CH_3OH} = 300 \text{ nm } (\epsilon = 37,000).$$

EXAMPLE XX

Preparation of (2,4-distearoxy-s-triazinyl-6-)methylcyanoacetate

To 600 ml of methanol there were added 71 g (3.08 moles) of sodium. After the sodium had been converted, methanol was evaporated just until the sodium methoxide formed began to precipitate. Subsequently, toluene was added and the remainder of the methanol was distilled off azeotropically. To the resulting suspension there were added dropwise 305 g (3.08 moles) of methylcyanoacetate, after which the methanol formed was distilled off azeotropically.

To the reaction mixture there were subsequently added at 40° C. 1000 g (1.54 moles) of 2,4-distearoxy-6-chloro-s-triazine, followed by boiling for one hour with refluxing. The toluene was then isolated from the reaction mixture followed by adding 4000 ml of methylene chloride. The reaction mixture was neutralized with 4 N hydrochloric acid. The organic layer was isolated, washed with water until neutral, dried and concentrated by evaporation. The resulting precipitate was treated with petroleum ether (boiling point 60°-80° C.), after which the product could be filtered off. After recrystallization from petroleum ether (boiling point 60°-80° C.) 1000 g of 2,4-distearoxy-s-triazinyl-6-methylcyano acetate were obtained in 90% yield.

EXAMPLE XXI

Preparation of (2-diethylamino-4-phenoxy-s-triazinyl-6-) methylcyanoacetate

A solution of 3.0 g (0.0083 moles) in 50 ml of chloroform of the diphenoxy compound prepared in accordance with Example IX was added dropwise at room temperature to a solution of 0.81 g (0.011 moles) of diethylamine in 20 ml of chloroform. Subsequently, the reaction mixture was refluxed for 1½ hours. The solvent was evaporated, after which the resulting oil was treated with ethyl acetate and a white precipitate was formed. This product was sucked off, washed with ethyl acetate and dried. Recrystallization from methanol gave 2.69 g of (2-diethylamino-4-phenoxy-s-triazinyl-6-)methylcyano acetate in 95% yield.

The melting point of the compound was between 201.9° and 202.6° C. The UV absorption was at $$\lambda_{max}^{CH_3OH} = 303 \text{ nm } (\epsilon = 36,600)$$

EXAMPLE XXII

Preparation of (2,4-dipiperidino-s-triazinyl-6-)methylcyanoacetate

The preparation was carried out starting from 3.0 g (0.0083 moles) of the (2,6-diphenoxy-s-triazinyl-6-)methylcyano acetate prepared in accordance with Example IX. In the same way as indicated in Example XXI, it was converted with 1.87 g (0.022 moles) of piperidine. The reaction product was treated with methanol. There were obtained 2.73 g of white crystalline (2,4-dipiperidino-s-triazinyl-6-)methylcyanoacetate in 96% yield.

The melting point of the compound was in the range of 243.2° to 243.7° C. The UV absorption maximum was at $$\lambda_{max}^{CH_3OH} = 300 \text{ nm } (\epsilon = 43,500)$$

EXAMPLE XXIII

Preparation of (2,4-dihydrazino-s-triazinyl-6-)methylcyanoacetate

To a solution of 1.4 g of hydrazine hydrate (80%; 0.022 moles) in 50 ml of 1,2-dimethoxyethane (DME) there was added dropwise a suspension in 50 ml of DME of 3.62 g (0.01 mole) of the (2,6-phenoxy-s-triazinyl-6-)methylcyanoacetate prepared in accordance with Example IX. The temperature was increased to boiling point, with all solid matter going into solution. After refluxing for 1 hour the resulting white precipitate (after cooling) was sucked off, washed with ether and dried, There were obtained 1.95 g of (2,4-dihydrazino-s-triazinyl-6-)methylcyanoacetate in 84% yield.

The melting point of the compound was above 300° C.

EXAMPLE XXIV

Preparation of (2,4-bis[2-hydroxyethylamino]-s-triazinyl-6-)methylcyanoacetate

The preparation was carried out starting from 3.62 g (0.01 mole) of the (2,6-diphenoxy-s-triazinyl-6-)methylcyanoacetate prepared in accordance with Example IX. In the same way as indicated in Example XXI it was converted with 2.68 g (0.044 moles) of ethanol amine. After refluxing for 4 hours the white precipitate, after cooling, was sucked off, washed with chloroform and ether, and dried. There were obtained 2.83 g of (2,4-bis[2-hydroxyethylamino]-s-triazinyl-6-)methylcyanoacetate in 96% yield.

The melting point of the compound was in the range of 238.7°–239.0° C. The UV absorption maximum was at $$\lambda_{max}^{(CH_3OH)} = 298 \text{ nm } (\epsilon = 39,800)$$

EXAMPLE XXV

Preparation of (2,4-bis[2-carbomethoxyethyl-mercapto]-s-triazinyl-6-)methylcyanoacetate As solution of 18.5 (0.1 mole) of cyanuric chloride in 70 ml of hot acetone was added dropwise to 70 ml of ice water. To the resulting suspension were added dropwise 24.0 g (0.2 moles) of β-mercapto-propionic methyl ester at a temperature of 0°–5° C. Subsequently, the reaction mixture was heated to room temperature followed by adding dropwise a solution of 11.0 g (0.1 mole) of sodium carbonate in 40 ml of water. After a reaction time of 1 hour at 35–40 the reaction mixture was extracted with chloroform. The extract was washed with water until neutral, dried, and concentrated by evaporation. There were obtained 32.7 g of 2,4 bis (2-carbomethoxyethyl-mercapto)-6-chloro-s-triazine in 93% yield.

To a suspension in toluene of sodium methanolate (prepared from 0.46 g (0.02 moles) of sodium) there was added dropwise a solution in toluene of 2.20 g (0.022 moles) of cyanoacetic methyl ester, after which the resulting methanol was distilled off azeotropically. The reaction mixture was cooled, after which there was added dropwise a solution in toluene of 3.51 g (0.01 mole) of 2,4 bis(2-carbomethoxyethylmercapto)-6-chloro-s-triazine. After refluxing for 3 hours the solvent was evaporated and the residue added to 150 ml of methylene chloride and 100 ml of 0.4 N hydrochloric acid. The organic layer was isolated and washed with water until neutral. After the organic solution had been dried and evaporated, an oil was obtained from which upon treatment with ether a crystalline product could be isolated. This product was recrystallized from methanol and there were obtained 3.20 g of (2,4-bis[2-carbomethoxyethylmercapto]-s-triazinyl-6-)methylcyanoacetate in 75% yield.

The melting point of the compound was between 107.2° and 109.5° C. The UV absorption maximum was at $$\lambda_{max}^{(CHCl_3)} = 287 \ nm \ (\epsilon = 32,100)$$

Shoulders at 294 nm and 330 nm.

EXAMPLE XXVI

Preparation of (2,4-bis[2-carbolauroxyethylmercapto]-s-triazinyl-6-)methylcyanoacetate 2,4-bis(2-carbolauroxyethylmercapto)-6-chloro-s-triazine was prepared as described in Example XXV. The preparation was was started from 18.5 g (0.1 mole) of cyanuric chloride, 55.0 g (0.2 moles) of β-mercaptopropionic lauryl ester and 11.0 g (0.1 mole) of sodium carbonate. Various treatments were finally followed by recrystallization from n-heptane, which resulted in obtaining 65 g of product in 98% yield.

The preparation of the compound mentioned in the heading was carried out as described in Example XXV. The preparation was started from 3.30 g (0.005 moles) of 2,4-bis(2-carbolauroxyethylmercapto)-6-chloro-s-triazine, 1.10 g (0.011 moles) of methylcyanoacetate and 0.01 mole of sodium methanolate prepared from 0.23 g (0.01 mole) of sodium. The resulting (2,4-bis-[2-carbolauroxyethylmercapto]-s-triazinyl-6-)methylcyanoacetate was recrystallized from methanol, after which there were obtained 2.91 g of product in 88% yield.

The melting point of the compound was in the range of 83.7° to 85.0° C. The UV absorption maximum was at $$\lambda_{max.}^{(CHCl_3)} = 287 \ nm \ (\epsilon = 31,300)$$

Shoulders at 293 nm and 330 nm

EXAMPLE XXVII

Preparation of (2,4-dimethoxy-s-triazinyl-6-)cyanoacetamide

Starting from 3.51 g (0.02 moles) of 2,4-dimethoxy-6-chloro-s-triazine, the preparation of which is indicated in Example I. In the same way as described in Example I, the 2,4-dimethoxy-6-chloro-s-triazine was coverted with the reaction product of 3.36 g (0.04 moles) of cyanoacetamide and 0.96 g (0.04 moles) of sodium hydride. After the reaction mixture had been poured into dilute hydrochloric acid, the precipitate sucked off, washed with water until neutral and dried. There were obtained 3.1 g of (2,4-dimethoxy-s-triazinyl-6-)cyanoacetamide in 70% yield.

The melting point of the compound was in the range of 259.2° to 260.7° C. The UV absorption maximum was at $$\lambda_{max}^{(CH_3OH)} = 301 \ nm \ (\epsilon = 30,500)$$

EXAMPLE XXVIII

Preparation of (2,4-dimethoxy-s-triazinyl-6-)phenylcyanoacetate

Starting from 2.63 g (0.015 moles) of 2,4-dimethoxy-6-chloro-s-triazine prepared in accordance with Example I. In the same way as indicated in Example I the 2,4-dimethoxy-6-chloro-s-triazine was converted with the reaction product of 5.0 g (0.031) moles of phenylcyanoacetate (prepared in accordance with the method described by E. Ziegler et al. in Monatshefte f.Chemie, 88, 164 (1957)) and 0.75 g (0.031 moles) of sodium hydride. The reaction product was poured into dilute hydrochloric acid and the precipitate obtained was sucked off, washed with water until neutral and dried. After recrystallization from methanol there were obtained 1.8 g of (2,4-dimethoxy-s-triazinyl-6-)phenylcyanoacetate in 40% yield.

The melting point of the compound was in the range of 185.0° to 185.2° C. The UV absorption maximum was at $$\lambda_{max}^{(CH_3OH)} = 300 \ nm \ (\epsilon = 37,000)$$

EXAMPLE XXIX 100 g of rigid polyvinyl chloride (marketed by Imperial Chemical Industries, ICI, under the trade name Corvic D 55/09), 1 g of stearyl alcohol, 1.5 g of dibutyl tin bis(methylmaleate) and 0.2 g of the UV absorption agent to be examined were processed into thin film on an oil-heated roll for 5 minutes. This film was pressed on a steam-heated roll for 2 minutes at 180° C. in order to remove the asperities in the film surface. Samples of film thus obtained were for different times exposed to UV radiation in a Xeno tester. The degradation was determined visually and rated from 0 to 4. The value 0 indicates that there has been no degradation; the value 1 stands for little degradation and the value 2 for moderate degradation. The rating 3 is indicative of strong discoloration and the rating 4 indicates that the film has become black.

The test results of the experiments with the various substances are given in the following two tables.

| No. | of the UV stabilizer |
|---|---|
| 1 | control |
| 2 | a compound marketed by Ciba-Geigy under the trade name Tinuvin P, and of the formula: (see below) |
| 3 | (2,4-dimethoxy-s-triazinyl-6-)methyl cyanoacetate |
| 4 | (2,4-diphenyl-s-triazinyl-6-)methyl cyanoacetate |
| 5 | (2,4-dilauroxy-s-triazinyl-6-)methyl cyanoacetate |
| 6 | (2,4-diphenoxy-s-triazinyl-6-)malodinitrile |
| 7 | (2,4-dimethoxy-s-triazinyl-6-)malodinitrile |
| 8 | (2-hydroxy, 4-methoxy-s-triazinyl-6-)malonic diethyl ester |
| 9 | (2,4-dimethoxy-s-triazinyl-6-)cyano-p-toluyl methane |

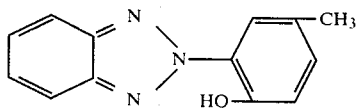

The substances 8 and 9 do not comply with the criterion of the present invention and are included for comparison.

Table II

| Sample with substance no. | Hours of Exposure | | | | |
|---|---|---|---|---|---|
| | 215 | 477 | 93 | 1169 | 1430 |
| 1 | 0 | 1 | 1 | 1 | 1 |
| 2 | 0 | 0 | 0 | 0 | 0 |
| 3 | 0 | 0 | 0 | 0 | 0 |
| 4 | 0 | 0 | 0 | 0 | 0 |
| 5 | 0 | 0 | 0 | 0 | 0 |
| 6 | 0 | 0 | 0 | 0 | 0 |

Table III

| Sample with substance no. | Hours of Exposure | | | | | |
|---|---|---|---|---|---|---|
| | 142 | 352 | 563 | 794 | 1011 | 1312 |
| 1 | 1 | 1 | 1 | 2 | 2 | 2 |
| 2 | 0 | 0 | 0 | 0 | 0 | 0 |
| 3 | 0 | 0 | 0 | 0 | 0 | 0 |
| 7 | 0 | 0 | 0 | 0 | 0 | 0 |
| 8 | 0 | 0 | 0 | 1 | 1 | 1 |
| 9 | 1 | 1 | 1 | 2 | 2 | 2 |

| Sample with substance no. | Hours of Exposure | | | | |
|---|---|---|---|---|---|
| | 1576 | 1833 | 1890 | 2196 | 2413 |
| 1 | 2 | 2 | 2 | 2 | 2 |
| 2 | 0 | 0 | 0 | 0 | 0 |
| 3 | 0 | 0 | 0 | 0 | 0 |
| 7 | 0 | 0 | 0 | 0 | 0 |
| 8 | 1 | 1 | 1 | 1 | 1 |
| 9 | 2 | 2 | 2 | 2 | 2 |

The results given in the above tables clearly show that the UV stabilizers 3 through 7 have the same stabilizing effect as the known Tinuvin P (substance 2).

It is obvious that the substances 8 and 9, whose structure very much resembles that of the substances according to the invention, have no or hardly any stabilizing effect.

EXAMPLE XXX

To 5 g of polypropylene powder marketed by ICI under the trade name HF 20 (without any addition of stabilizer) there was added a solution in an organic solvent (preferably chloroform) of the UV stabilizer to be investigated.

The solvent was removed from this slurry by evaporation, with stirring, over a period of about 2 hours at 50° C. The product obtained was dried for 3 hours at 80° C. Over a period of 3 minutes and at 190° C. the resulting powder was pressed into a film 150 mμ thick. Samples of the film thus obtained were exposed to UV radiation in a type 150 Xeno-testing apparatus over various periods. The moment at which the film becomes brittle was determined by bending the film through 180°. The results of the experiments with the various substances are given in the following table.

---

No. of the UV stabilizer

1. Control
2. A compound marketed by Ciba-Geigy Co. under the trade name Tinuvin 327, of the formula:

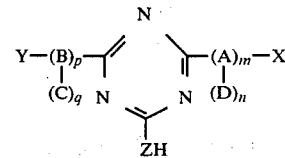

3. (2,4-bis[2-carbomethylethylmercapto]-s-triazinyl-6-)methylcyanoacetate.
4. (2,4-bis[2-carbolauroxyethylmercapto]-s-triazinyl-6-)methylcyanoacetate.

| Sample substance no. | Exposure time after which film breaks upon bending through 180° |
|---|---|
| 1 | 120 hours |
| 2 | 430 hours |
| 3 | 410 hours |
| 4 | 750 hours |

What is claimed is:
1. A compound of the formula:

$$Y-(B)_p-\underset{(C)_q}{\overset{N}{\diagup}}\underset{N}{\overset{}{\diagdown}}\underset{ZH}{\overset{}{\diagup}}\underset{(D)_n}{\overset{}{\diagdown}}-X$$

wherein m, n, p, and q are independently 0 or 1, provided that n=0 if m=0 and q=0 if p=0; when m=0, X is selected from the group consisting of chlorine, ZH, alkyl having 1 to 20 carbon atoms, alkenyl having 2 to 20 carbon atoms, cycloalkyl having 3 to 6 carbon atoms, and phenyl; when m=1 and n=0, X is selected from the group consisting of alkyl having 1 to 20 carbon atoms, alkenyl having 2 to 20 carbon atoms, cycloalkyl having 3 to 6 carbon atoms, and phenyl; when m=1 and n=1, X is selected from the group consisting of hydrogen, alkanoyl having 2 to 20 carbon atoms, benzoyl, benzene sulphonyl, amino, monoalkylamine having 2 to 8 carbon atoms, dialkylamino having 2 to 8 carbon atoms, phenylamino, alkyl having 1 to 20 carbon atoms, alkenyl having 2 to 20 carbon atoms, cycloalkyl having 3 to 6 carbon atoms, and phenyl; when p=0, Y is selected from the group consisting of ZH, alkyl having 1 to 20 carbon atoms, alkenyl having 2 to 20 carbon atoms, cycloalkyl having 3 to 6 carbon atoms, and phenyl; when p=1 and q=0, Y is selected from the group consisting of alkyl having 1 to 20 carbon atoms, alkenyl having 2 to 20 carbon atoms, cycloalkyl having 3 to 6 carbon atoms, and phenyl; when p=1 and q=1, Y is selected from the group consisting of hydrogen, alkanoyl having 2 to 20 carbon atoms, benzoyl, benzene sulphonyl, amino, monoalkylamino having 2 to 8 carbon atoms, dialkylamino having 2 to 8 carbon atoms, phenylamino, alkyl having 1 to 20 carbon atoms, alkenyl having 2 to 20 carbon atoms, cycloalkyl having 3 to 6 carbon atoms, and phenyl; when m=1 and n=1, A is nitrogen; when p=1 and q=1, B is nitrogen; when m=1 and n=0, A is oxygen or sulfur; when p=1 and q=0, B is oxygen or sulfur; when p=1 and q=1, C is selected from the group consisting of hydrogen, alkyl having 1 to 20 carbon atoms, alkenyl having 2 to 20 carbon atoms, cycloalkyl having 3 to 6 carbon atoms, and phenyl; when n=1 and m=1, D is selected from the group consisting of hydrogen, alkyl having 1 to 20 carbon atoms, alkenyl having 2 to 20 carbon atoms, cycloalkyl having 3 to 6 carbon atoms, and phenyl; the groups Y, B, and C being capable of forming a heterocyclic ring having 2 to 5 carbon atoms in which B represents the hetero nitrogen atom; the groups X, A, and D being capable of forming a heterocyclic ring having 2 to 5 carbon atoms in which A represents the hetero nitrogen atom; in all instances ZH represents a group which may lose a hydrogen atom in favor of an adjacent nitrogen atom of the triazine ring to form a desmotropic structure of the formula:

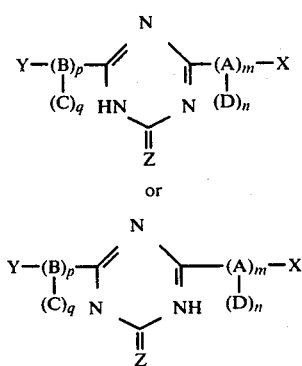

Z is in all instances a group of the formula

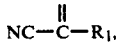

in which $R_1$ is selected from the group consisting of CN,

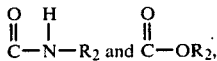

wherein $R_2$ is selected from the group consisting of hydrogen, alkyl, aralkyl, and cycloalkyl.

2. (2,4-diallyl-s-triazinyl-6-)methyl cyanoacetate.
3. (2,4-dimethoxy-s-triazinyl-6-)methyl cyanoacetate.
4. (2,4-dioctoxy-s-triazinyl-6-)methyl cyanoacetate.
5. (2,4-dilauroxy-s-triazinyl-6-)methyl cyanoacetate.
6. (2,4-distearoxy-s-triazinyl-6-)methyl cyanoacetate.
7. (2,4-dimethoxy-s-triazinyl-6-)lauryl cyanoacetate.
8. (2,4-dimethoxy-s-triazinyl-6-)benzyl cyanoacetate.
9. (2,4-dioctoxy-s-triazinyl-6-)benzyl cyanoacetate.
10. (2,4-dimethylthio-s-triazinyl-6-)methyl cyanoacetate.
11. (2,4-diphenoxy-s-triazinyl-6-)methyl cyanoacetate.
12. (2,4-bis[4-methoxyphenoxy-]-s-triazinyl-6-)methyl cyanoacetate.
13. (2,4-diphenyl-s-triazinyl-6-)methyl cyanoacetate.
14. (2,4-dimethoxy-s-triazinyl-6-)malodinitrile.
15. (2,4-dioctoxy-s-triazinyl-6-)malodinitrile.
16. (2,4-dilauroxy-s-triazinyl-6-)malodinitrile.
17. (2,4-distearoxy-s-triazinyl-6-)malodinitrile.
18. (2,4-dimethylthio-s-triazinyl-6-)malodinitrile.
19. (2,4-diphenoxy-s-triazinyl-6-)malodinitrile.
20. (2,4-di-(carbomethoxycyanomethyl)-6-methoxy-s-triazine.
21. (2,4-dimethoxy-s-triazinyl-6-)phenyl cyanoacetate.
22. (2-diethylamino-4-phenoxy-s-triazinyl-6-)methyl cyanoacetate.
23. (2,4-dipiperidino-s-triazinyl-6-)methyl cyanoacetate.
24. (2,4-dihydrazino-s-triazinyl-6-)methyl cyanoacetate.
25. (2,4-bis[2-carbomethoxyethylmercapto]-s-triazinyl-6-)methyl cyanoacetate.
26. (2,4-bis[2 carbolauroxyethylmercapto]-s-triazinyl-6-)methyl cyanoacetate.
27. (2,4-dimethoxy-s-triazinyl-6-)cyanoacetamide.
28. (2,4-bis(2-hydroxyethylamino)-s-triazinyl-6-)methyl cyanoacetate.

* * * * *